US010316368B2

(12) United States Patent
Klumpp et al.

(10) Patent No.: US 10,316,368 B2
(45) Date of Patent: Jun. 11, 2019

(54) ALTERED MICROBIOME OF CHRONIC PELVIC PAIN

(71) Applicants: Northwestern University, Evanston, IL (US); The Board of Trustees of the University of Illinois, Urbana, IL (US)

(72) Inventors: David J. Klumpp, Chicago, IL (US); Anthony J. Schaeffer, Hinsdale, IL (US); Bryan A. White, Champaign, IL (US)

(73) Assignees: Northwestern University, Evanston, IL (US); The Board of Trustees of the University of Illinoi, Urbana, IL (US)

( * ) Notice: Subject to any disclaimer, the term of this patent is extended or adjusted under 35 U.S.C. 154(b) by 0 days.

(21) Appl. No.: 15/729,249

(22) Filed: Oct. 10, 2017

(65) Prior Publication Data

US 2018/0087094 A1 Mar. 29, 2018

Related U.S. Application Data

(62) Division of application No. 14/677,239, filed on Apr. 2, 2015, now Pat. No. 9,783,858.

(60) Provisional application No. 61/974,277, filed on Apr. 2, 2014.

(51) Int. Cl.
| | | |
|---|---|---|
| *A61K 35/00* | (2006.01) | |
| *A61K 35/74* | (2015.01) | |
| *C12Q 1/689* | (2018.01) | |
| *A61K 35/741* | (2015.01) | |
| *C12Q 1/6883* | (2018.01) | |

(52) U.S. Cl.
CPC ............. *C12Q 1/689* (2013.01); *A61K 35/74* (2013.01); *A61K 35/741* (2013.01); *C12Q 1/6883* (2013.01); *A61K 2035/115* (2013.01)

(58) Field of Classification Search
None
See application file for complete search history.

(56) References Cited

U.S. PATENT DOCUMENTS

2010/0247489 A1* 9/2010 Saur-Brosch ........ A61K 9/2846
424/93.4
2015/0246081 A1* 9/2015 Morris ................. A61K 35/744
424/93.41
2015/0284781 A1 10/2015 Klumpp et al.

FOREIGN PATENT DOCUMENTS

WO WO-2014121302 A2 * 8/2014 ............. A61K 35/74

OTHER PUBLICATIONS

Ait-Belgnaoui et al., Prevention of gut leakiness by a probiotic treatment leads to attenuated HPA response to an acute psychological stress in rats. Psychoneuroendocrinology, 2012. 37(11):1885-95.
Braundmeier-Fleming et al., Altered Microbiome in Chronic Pelvic Pain Patients, Abstract, presented at Keystone Symposia on Molecular and Cellular Biology, Apr. 1-6, 2014, Big Sky, Montana, 1 page.
Braundmeier-Fleming et al., Altered Microbiome in Chronic Pelvic Pain Patients, Poster, presented at Keystone Symposia on Molecular and Cellular Biology, Apr. 1-6, 2014, Big Sky, Montana, 1 page.
Bravo et al., Ingestion of Lactobacillus strain regulates emotional behavior and central GABA receptor expression in a mouse via the vagus nerve. Proc Natl Acad Sci U S A, 2011. 108(38):16050-5.
Buccafusco, Methods of Behavior Analysis in Neuroscience. 2nd ed. 2008: CRC Press, TOC only, 16 pages.
Cambronero et al., Role of arachidonic acid metabolism on corticotropin-releasing factor (CRF)-release induced by interleukin-1 from superfused rat hypothalami. J Neuroimmunol, 1992. 39(1-2):57-66.
Chen et al., RANTES mediates TNF-dependent lamina propria mast cell accumulation and barrier dysfunction in neurogenic cystitis. Am J Physiol Renal Physiol, 2007. 292(5):F1372-9.
Chen et al., Urothelial lesion formation is mediated by TNFR1 during neurogenic cystitis. Am J Physiol Renal Physiol, 2006. 291(4):F741-9.
Elliott et al., Resilience to social stress coincides with functional DNA methylation of the Crf gene in adult mice. Nat Neurosci, 2010. 13(11):1351-3.
Erwin et al., Deacylation of structurally diverse lipopolysaccharides by human acyloxyacyl hydrolase. J Biol Chem, 1990. 265(27):16444-9.
Farmer et al., Brain functional and anatomical changes in chronic prostatitis/chronic pelvic pain syndrome. J Urol, 2011. 186(1):117-24.
Goodman et al., Extensive personal human gut microbiota culture collections characterized and manipulated in gnotobiotic mice. Proc Natl Acad Sci U S A. Apr. 12, 2011;108(15):6252-7.
Group Jumpstart Consortium Human Microbiome Project Data Generation Working Group (2012) Evaluation of 16S rDNA-Based Community Profiling for Human Microbiome Research. PLoS One 7(6): e39315.
Guo et al., The innate immunity of the central nervous system in chronic pain: the role of Toll-like receptors. Cell Mol Life Sci, 2007. 64(9):1128-36.
Gustafsson and A.B. Maunsbach, Ultrastructure of the enlargec cecum in germfree rats. Z Zellforsch Mikrosk Anat, 1971. 120(4):555-78.
Hagen et al., Expression and characterization of recombinant human acyloxyacyl hydrolase, a leukocyte enzyme that deacylates bacterial lipopolysaccharides. Biochemistry, 1991. 30(34):8415-23.

(Continued)

*Primary Examiner* — Brian Gangle

(74) *Attorney, Agent, or Firm* — Casimir Jones SC; David W. Staple

(57) ABSTRACT

Provided herein are kits, compositions, and methods for diagnosing and treating interstitial cystitis (IC) and/or interstitial cystitis/bladder pain syndrome (IC/BPS) based on finding lower levels of certain bacteria in a subject's stool sample (e.g., *O. splanchnicus, F. prausnitzii, C. aerofaciens, E. sinensis, L. longoviformis,* and *R. intestinalis*). In certain embodiments, then present invention provides probiotic formulations containing live bacteria (e.g., from *O. splanchnicus, F. prausnitzii, C. aerofaciens, E. sinensis, L. longoviformis,* and *R. intestinalis*).

7 Claims, 3 Drawing Sheets

Specification includes a Sequence Listing.

(56) References Cited

OTHER PUBLICATIONS

Hanno et al., AUA guideline for the diagnosis and treatment of interstitial cystitis/bladder pain syndrome. J Urol, 2011. 185(6):2162-70.
Kageyama et al., Regulatory mechanisms underlying corticotropin-releasing factor gene expression in the hypothalamus. Endocr J, 2009. 56(3):335-44.
Klausner et al., Corticotropin releasing factor: a mediator of emotional influences on bladder function. J Urol, 2004. 172(6 Pt 2):2570-3.
Klumpp et al., Summation model of pelvic pain in interstitial cystitis. Nat Clin Pract Urol, 2008. 5(9):494-500.
Laird et al., A new model of visceral pain and referred hyperalgesia in the mouse. Pain, 2001. 92(3):335-42.
Laird et al., Deficits in visceral pain and referred hyperalgesia in Nav1.8 (SNS/PN3)-null mice. J Neurosci, 2002. 22(19):8352-6.
Langille et al., Predictive functional profiling of microbial communities using 16S rRNA marker gene sequences, Nat Biotechnol. Sep. 2013;31(9):814-21.
Lutgendorf et al., Stress and symptomatology in patients with interstitial cystitis: a laboratory stress model. J Urol, 2000. 164(4):1265-9.
Magalhaes et al., CRF receptor 1 regulates anxiety behavior via sensitization of 5-HT2 receptor signaling. Nat Neurosci, 2010. 13(5):622-9.
Malykhina et al., Differential effects of intravesical resiniferatoxin on excitability of bladder spinal neurons upon colon-bladder cross-sensitization. Brain Res, 2013. 1491:213-24.
Malykhina, Neural mechanisms of pelvic organ cross-sensitization. Neuroscience, 2007. 149(3):660-72.
Morgan et al., Dysfunction of the intestinal microbiome in inflammatory bowel disease and treatment. Genome Biol, 2012. 13(9):R79.
Munford et al., Acyloxyacyl hydrolase, a leukocyte enzyme that deacylates bacterial lipopolysaccharides, has phospholipase, lysophospholipase, diacylglycerollipase, and acyltransferase activities in vitro. J Biol Chem, 1992. 267(14):10116-21.
Munford et al., Purification of acyloxyacyl hydrolase, a leukocyte enzyme that removes secondary acyl chains from bacterial lipopolysaccharides. J Biol Chem, 1989. 264(26):15613-9.
Paez-Pereda et al., Corticotropin releasing factor receptor antagonists for major depressive disorder. Expert Opin Investig Drugs, 2011. 20(4):519-35.
Parsons et al., The role of urinary potassium in the pathogenesis and diagnosis of interstitial cystitis. J Urol, 1998. 159(6):1862-6; discussion 1866-7.
Pezzone et al., A model of neural cross-talk and irritation in the pelvis: implications for the overlap of chronic pelvic pain disorders. Gastroenterology, 2005. 128(7):1953-64.
Rosen et al., Mechanisms of pain from urinary tract infection.Int J Urol. Apr. 2014;21 Suppl 1:26-32.
Rudick et al., A role for the basal forebrain cholinergic system in estrogen-induced disinhibition of hippocampal pyramidal cells. J Neurosci, 2003. 23(11):4479-90.
Rudick et al., Gender specific pelvic pain severity in neurogenic cystitis. J Urol, 2012. 187(2):715-24.
Rudick et al., Host-pathogen interactions mediating pain of urinary tract infection. J Infect Dis, 2010. 201(8):1240-9.
Rudick et al., Mast cell-derived histamine mediates cystitis pain. PLoS One, 2008. 3(5):e2096.
Rudick et al., O-antigen modulates infection-induced pain states. PLoS One, 2012. 7(8):e41273.
Rudick et al., Organ Crosstalk Modulates Pelvic Pain. Am J Physiol Regul Integr Comp Physiol, 2007. 293(3):R1191-8.
Rudick et al., Pharmacologic attenuation of pelvic pain in a murine model of interstitial cystitis. BMC Urol, 2009. 9:16.
Rudick et al., Uropathogenic *Escherichia coli* induces chronic pelvic pain. Infect Immun, 2011. 79(2):628-35.
Scholz et al., The neuropathic pain triad: neurons, immune cells and glia. Nat Neurosci, 2007. 10(11):1361-8.
Shao et al., Prolonged hepatomegaly in mice that cannot inactivate bacterial endotoxin. Hepatology, 2011. 54(3):1051-62.
Shorter et al., Effect of comestibles on symptoms of interstitial cystitis. J Urol, 2007. 178(1):145-52.
Sun et al., Stress-induced corticotropin-releasing hormone-mediated NLRP6 inflammasome inhibition and transmissible enteritis in mice. Gastroenterology, 2013. 144(7):1478-87, 1487 e1-8.
Valentino et al., Pontine regulation of pelvic viscera: pharmacological target for pelvic visceral dysfunctions. Trends Pharmacol Sci, 1999. 20(6):253-60.
Valentino et al., The bladder-brain connection: putative role of corticotropin-releasing factor. Nat Rev Urol, 2011. 8(1):19-28.
Warren et al., Urinary tract infection and inflammation at onset of interstitial cystitis/painful bladder syndrome. Urology, 2008. 71(6):1085-90.
Yang et al., Ca2=/calmodulin-dependent protein kinase II is associated with pelvic pain of neurogenic cystitis. Am J Physiol Renal Physiol, 2012. 303(3):F350-6.
Yeoman et al., A multi-omic systems-based approach reveals metabolic markers of bacterial vaginosis and insight into the disease. PLoS One, 2013. 8(2):e56111.

\* cited by examiner

SEQUENCE LISTING

<160> NUMBER OF SEQ ID NOS: 14

<210> SEQ ID NO 1
<211> LENGTH: 17
<212> TYPE: DNA
<213> ORGANISM: Artificial sequence
<220> FEATURE:
<223> OTHER INFORMATION: Synthetic

<400> SEQUENCE: 1
cctacgggag gcagcag                                                 17

<210> SEQ ID NO 2
<211> LENGTH: 18
<212> TYPE: DNA
<213> ORGANISM: Artificial sequence
<220> FEATURE:
<223> OTHER INFORMATION: Synthetic

<400> SEQUENCE: 2
ccgtcaattc mtttragt                                                18

<210> SEQ ID NO 3
<211> LENGTH: 20
<212> TYPE: DNA
<213> ORGANISM: Artificial sequence
<220> FEATURE:
<223> OTHER INFORMATION: Synthetic

<400> SEQUENCE: 3
tcgaaggctt gaccttacgc                                              20

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
ttcattcgta cgtccggtgg                                              20

<210> SEQ ID NO 5
<211> LENGTH: 20
<212> TYPE: DNA
<213> ORGANISM: Artificial sequence
<220> FEATURE:
<223> OTHER INFORMATION: Synthetic

<400> SEQUENCE: 5
gaggttgaac ggccacattg                                              20

<210> SEQ ID NO 6
<211> LENGTH: 20
<212> TYPE: DNA
<213> ORGANISM: Artificial sequence
<220> FEATURE:
<223> OTHER INFORMATION: Synthetic

<400> SEQUENCE: 6
acctagtaaa catcggccac                                              20

<210> SEQ ID NO 7
<211> LENGTH: 19
<212> TYPE: DNA
<213> ORGANISM: Artificial sequence

```
<220> FEATURE:
<223> OTHER INFORMATION: Synthetic

<400> SEQUENCE: 7
gtggaacacc gatggcgaa                                                    19

<210> SEQ ID NO 8
<211> LENGTH: 20
<212> TYPE: DNA
<213> ORGANISM: Artificial sequence
<220> FEATURE:
<223> OTHER INFORMATION: Synthetic

<400> SEQUENCE: 8
cctggtaagg ttcttcgcgt                                                   20

<210> SEQ ID NO 9
<211> LENGTH: 20
<212> TYPE: DNA
<213> ORGANISM: Artificial sequence
<220> FEATURE:
<223> OTHER INFORMATION: Synthetic

<400> SEQUENCE: 9
gggatctcta atccgagggc                                                   20

<210> SEQ ID NO 10
<211> LENGTH: 19
<212> TYPE: DNA
<213> ORGANISM: Artificial sequence
<220> FEATURE:
<223> OTHER INFORMATION: Synthetic

<400> SEQUENCE: 10
taatgcgtta gctgcgggc                                                    19

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11
tgcattggaa actgtgcagc                                                   20

<210> SEQ ID NO 12
<211> LENGTH: 20
<212> TYPE: DNA
<213> ORGANISM: Artificial sequence
<220> FEATURE:
<223> OTHER INFORMATION: Synthetic

<400> SEQUENCE: 12
ttcttgcgaa cgtactcccc                                                   20

<210> SEQ ID NO 13
<211> LENGTH: 20
<212> TYPE: DNA
<213> ORGANISM: Artificial sequence
<220> FEATURE:
<223> OTHER INFORMATION: Synthetic

<400> SEQUENCE: 13
cggcttaaat acgtgccagc                                                   20
```

```
<210> SEQ ID NO 14
<211> LENGTH: 20
<212> TYPE: DNA
<213> ORGANISM: Artificial sequence
<220> FEATURE:
<223> OTHER INFORMATION: Synthetic

<400> SEQUENCE: 14
agcctcagcg tcagtaatcg                                                     20
```

ALTERED MICROBIOME OF CHRONIC PELVIC PAIN

The present application is a divisional of U.S. patent application Ser. No. 14/677,239, filed Apr. 2, 2015, which claims priority to U.S. Provisional Application Ser. No. 61/974,277, filed Apr. 2, 2014, each of which is herein incorporated by reference in its entirety.

STATEMENT REGARDING FEDERAL FUNDING

This invention was made with government support under R24 DK094575 awarded by the National Institutes of Health. The government has certain rights in the invention.

FIELD OF THE INVENTION

Provided herein are kits, compositions, and methods for diagnosing and treating interstitial cystitis (IC) and/or interstitial cystitis/bladder pain syndrome (IC/BPS) based on finding lower levels of certain bacteria in a subject's stool sample (e.g., *O. splanchnicus, F. prausnitzii, C. aerofaciens, E. sinensis, L. longoviformis*, and *R. intestinalis*). In certain embodiments, then present invention provides probiotic formulations containing live bacteria (e.g., from *O. splanchnicus, F. prausnitzii, C. aerofaciens, E. sinensis, L. longoviformis*, and *R. intestinalis*).

BACKGROUND

Urologic chronic pelvic pain syndromes (UCPPS) debilitate millions of patients in the U.S., yet the etiologies are unknown, and no effective therapies or diagnostic markers exist. Interstitial cystitis/bladder pain syndrome (IC/BPS or IC) primarily afflicts women with severe pelvic pain, voiding dysfunction, and depression, and men with chronic prostatitis/chronic pelvic pain syndrome (CP/CPPS) are similarly afflicted. Many potential UCPPS mechanisms have been studied—including infection, inflammation, neurogenic dysfunction, and hypothalamic-pituitary-adrenal (HPA) axis dysregulation—but no mechanism associates with more than a subset of patients.

SUMMARY OF THE INVENTION

Provided herein are kits, compositions, and methods for diagnosing and treating interstitial cystitis (IC) and/or interstitial cystitis/bladder pain syndrome (IC/BPS) based on finding lower levels of certain bacteria in a subject's stool sample (e.g., *O. splanchnicus, F. prausnitzii, C. aerofaciens, E. sinensis, L. longoviformis*, and *R. intestinalis*). In certain embodiments, then present invention provides probiotic formulations containing live bacteria (e.g., from *O. splanchnicus, F. prausnitzii, C. aerofaciens, E. sinensis, L. longoviformis*, and *R. intestinalis*).

In some embodiments, provided herein are methods comprising: a) testing, or having a sample (e.g., stool sample) from a subject tested, to determine the level of bacteria from at least one bacterial species from a bacterial genus compared to healthy control population levels, wherein said bacterial genus is selected from the group consisting of: *Odoribacter, Faecalibacterium, Colinsella, Eggerthella, Lactonifactor*, and *Roseburia*, and b) performing at least one of the following: i) generating a report that indicates that said subject has or is at risk of interstitial cystitis (IC) and/or interstitial cystitis/bladder pain syndrome (IC/BPS) based on finding a reduced level of said at least one bacterial species in said stool sample compared to said control; ii) generating a report that indicates that said subject does not have or is not at risk of IC and/or IC/BPS based on finding a non-reduced level of said at least one bacterial species in said stool sample compared to said control; iii) diagnosing and/or informing said subject that they have or are at risk for IC and/or IC/BPS based on finding a reduced level of said at least one bacterial species in said stool sample compared to said control; iv) informing said subject that they do not have or are not at risk for IC and/or IC/BPS based on finding a non-reduced level of said at least one bacterial species in said stool sample compared to said control; and v) prescribing and or administering a probiotic and/or therapeutic agent targeting IC and/or IC/BPS to said subject based on finding a reduced level of said at least one bacterial species in said stool sample compared to said control.

In certain embodiments, said at least one species is selected from the group consisting of: *Odoribacter splanchnicus, Faecalibacterium prausnitzii, Colinsella aerofaciens, Eggerthella sinensis, Lactonifactor longoviformis*, and *Roseburia intestinalis*. In further embodiments, said at least one species is at least two, at least three, at least four, at least five, all six, species selected from the group consisting of: *Odoribacter splanchnicus, Faecalibacterium prausnitzii, Colinsella aerofaciens, Eggerthella sinensis, Lactonifactor longoviformis*, and *Roseburia intestinalis*.

In particular embodiments, the stool sample is tested with a sequencing assay specific to ribosomal rRNA of said at least one species (e.g., conserved rRNA regions among a particular genus or species). In particular embodiments, the testing comprises the use of a PCR assay, sequencing assay, or ELISA type assay. In further embodiments, the subject has symptoms of IC and/or IC/BPS. In further embodiments, said probiotic comprises live bacteria from said at least one species (e.g., from at least one, two, three, four, five, or all six of said species of bacteria). In particular embodiments, therapeutic agent comprises a stool specimen from a healthy individual (e.g., gut flora from a healthy person is transferred, for example by enema, to a subject with IC or IC/BPS symptoms).

In certain embodiments, provided herein are methods of comprising: a) having a sample (e.g., stool sample) from a subject with symptoms IC or IC/BPS tested to determine the level of bacteria from at least one species of bacteria from a genus of bacteria compared to healthy control population levels, wherein said subject has symptoms of interstitial cystitis (IC) and/or interstitial cystitis/bladder pain syndrome (IC/BPS), and wherein said genus of bacteria is selected from the group consisting of: *Odoribacter, Faecalibacterium, Colinsella, Eggerthella, Lactonifactor*, and *Roseburia*, and b) administering a probiotic or therapeutic agent targeting IC and/or IC/BPS to said subject such that at least one of said symptoms of IC and/or IC/BPS is reduced or eliminated.

In particular embodiments, provided herein are compositions comprising: i) a capsule formulated for human consumption, and ii) a probiotic formulation contained within said capsule, wherein said probiotic formulation comprises live bacteria from at least one species from a genus of bacteria, wherein said genus of bacteria is selected from the group consisting of: *Odoribacter, Faecalibacterium, Colinsella, Eggerthella, Lactonifactor*, and *Roseburia*. In certain embodiments, the at least one species is selected from the group consisting of: *Odoribacter splanchnicus, Faecalibacterium prausnitzii, Colinsella aerofaciens, Eggerthella sinensis, Lactonifactor longoviformis*, and *Roseburia intesti-* nalis. In some embodiments, the at least one species is at least two, three, four, five, or all six, species selected from the group consisting of: *Odoribacter splanchnicus, Faecalibacterium prausnitzii, Colinsella aerofaciens, Eggerthella sinensis, Lactonifactor longoviformis,* and *Roseburia intestinalis.*

In particular embodiments, provided herein are systems comprising: i) a report that indicates that said subject has or is at risk of interstitial cystitis (IC) and/or interstitial cystitis/bladder pain syndrome (IC/BPS) based on finding a reduced level of at least one species of bacteria from a genus of bacteria in said stool sample compared to said control, wherein said genus of bacteria is selected from the group consisting of: *Odoribacter, Faecalibacterium, Colinsella, Eggerthella, Lactonifactor,* and *Roseburia*; and ii) a probiotic or therapeutic agent targeting IC and/or IC/BPS. In certain embodiments, the probiotic comprises live bacteria from said genus of bacteria. In additional embodiments, the at least one species is selected from the group consisting of: *Odoribacter splanchnicus, Faecalibacterium prausnitzii, Colinsella aerofaciens, Eggerthella sinensis, Lactonifactor longoviformis,* and *Roseburia intestinalis.* In certain embodiments, the at least one species is at least two, three, four, five, or all six species selected from the group consisting of: *Odoribacter splanchnicus, Faecalibacterium prausnitzii, Colinsella aerofaciens, Eggerthella sinensis, Lactonifactor longoviformis,* and *Roseburia intestinalis.*

In some embodiments, provided herein are systems and compositions comprising: a) first diagnostic reagents able to detect a first species of bacteria from a genus of bacteria, wherein said genus of bacteria are selected from the group consisting of: *Odoribacter, Faecalibacterium, Colinsella, Eggerthella, Lactonifactor,* and *Roseburia*; and b) second diagnostic reagents able to detect a second species from a genus of bacteria, wherein said second species is different from said first species, and wherein said genus of bacteria is selected from the group consisting of: *Odoribacter, Faecalibacterium, Colinsella, Eggerthella, Lactonifactor,* and *Roseburia.*

In particular embodiments, the first and second species of bacteria are selected from the group consisting of: *Odoribacter splanchnicus, Faecalibacterium prausnitzii, Colinsella aerofaciens, Eggerthella sinensis, Lactonifactor longoviformis,* and *Roseburia intestinalis.* In other embodiments, said first and second diagnostic reagents comprise primer pairs, or nucleic acid probes, specific for said first and second species of bacteria respectively. In further embodiments, the first and second diagnostic reagents comprise antibodies specific for said first and second species of bacteria respectively. In particular embodiments, said first and second diagnostic reagents are in separate wells of a multi-well plate.

In certain embodiments of all of the above, bacterial species are substituted in that are higher, rather than lower (so all the correlations are the opposite of the above), in patients suspected of having IC or IC/BPS. Examples of such species are *Lachnospiriceae pectinoschiz* and *Egerthella lenta* (see FIG. 2).

In other embodiments of any of the above, at least one of the following genera or species are substituted in, wherein the genera or species is selected from: *Actinobacteria Eggerthella, Faecalibacterium, Lactonifactor, Lachnospiracea incertae sedis, Clostridium, Collinsella, Roseburia, Dorea, Blautia, Proteobacteria Escherichia Shigella, Streptococcus, Lachnospiracea incertae sedis, Flavonifractor, Blautia, Lachnospiracea incertae sedis, Anaerostipes, Erysipelotrichaceae incertae sedis, Lachnospiracea incertae sedis, Anaerofilum, Anaerofustis, Faecalibacterium, Faecalibacterium, Lachnospiracea incertae sedis,* and *Alkalibaculum* 1200.

In some embodiments, provided here are methods comprising: a) testing or having a sample (e.g., stool sample) from a subject tested to determine the level of bacteria from the *Odoribacter* genus compared to healthy control population levels, and b) performing at least one of the following: i) generating a report that indicates that the subject has or is at risk of interstitial cystitis (IC) and/or interstitial cystitis/bladder pain syndrome (IC/BPS) based on finding a reduced level of *Odoribacter* in the sample compared to the control; ii) generating a report that indicates that the subject does not have or is not at risk of IC and/or IC/BPS based on finding a non-reduced level of *Odoribacter* in the sample compared to the control; iii) diagnosing and/or informing the subject that they have or are at risk for IC and/or IC/BPS based on finding a reduced level of *Odoribacter* in the sample compared to the control; iv) informing the subject that they do not have or are not at risk for IC and/or IC/BPS based on finding a non-reduced level of *Odoribacter* in the sample compared to the control; and v) prescribing and or administering a probiotic and/or therapeutic agent targeting IC and/or IC/BPS to the subject based on finding a reduced level of *Odoribacter* in the sample compared to the control.

In certain embodiments, the sample is a stool sample. In particular, embodiments, the stool sample is tested with a sequencing assay specific to ribosomal rRNA. In other embodiments, the sample is tested with a PCR assay specific for *Odoribacter*, or an antibody assay specific for *Odoribacter*. In other embodiments, the subject has symptoms of IDC and/or IC/BPS. In further embodiments, is electronic (e.g., displayed on a GUI) or on paper. In other embodiments, the probiotic comprises live *Odoirbacter* bacteria. In further embodiments, the therapeutic agent comprises an antibiotic. In additional embodiments, the therapeutic comprises antibodies that bind MCP-1 or MIP-1α. In additional embodiments, the therapeutic agent comprises a stool specimen from a healthy individual. In additional embodiments, the subject is a female human. In other embodiments, the subject is a male human.

In certain embodiments, provided herein are methods comprising: a) having a stool sample from a subject with symptoms of tested to determine the level of bacteria from the *Odoribacter* genus compared to healthy control population levels, wherein the subject has symptoms of interstitial cystitis (IC) and/or interstitial cystitis/bladder pain syndrome (IC/BPS), and b) administering a probiotic or therapeutic agent targeting IC and/or IC/BPS to the subject such that at least one of the symptoms of IC and/or IC/BPS is reduced or eliminated.

In some embodiments, the present invention provides compositions comprising: i) a capsule formulated for human consumption, and ii) a probiotic formulation contained within the capsule, wherein the probiotic formulation comprises live bacteria of the genus *Odoribacter*. In further embodiments, the provided herein are kits or systems comprising: i) a report that indicates that the subject has or is at risk of interstitial cystitis (IC) and/or interstitial cystitis/bladder pain syndrome (IC/BPS) based on finding a reduced level of *Odoribacter* in the stool sample compared to the control; ii) a probiotic or therapeutic agent targeting IC and/or IC/BPS.

DESCRIPTION OF THE FIGURES

FIG. 1B shows results of Example 1 where pain was assessed in a mouse model, comparing mice with healthy flora vs. mice with IC flora.

DETAILED DESCRIPTION

Figure 1A:
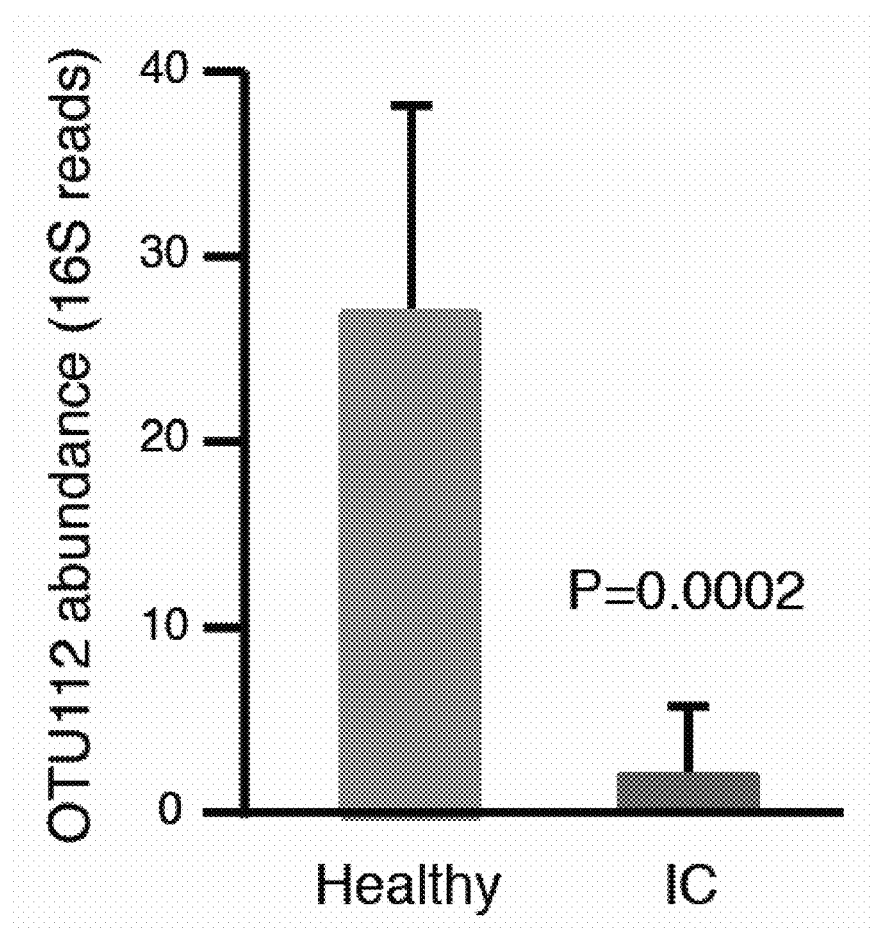
FIGS. 1A-B show results of Example 1 where analyses of stool microbiota revealed OTU112, *Odoribacter*, as a taxon significantly reduced in IC patients.

Provided herein are kits, compositions, and methods for diagnosing and treating interstitial cystitis (IC) and/or interstitial cystitis/bladder pain syndrome (IC/BPS) based on finding lower levels of certain bacteria in a subject's stool sample (e.g., *O. splanchnicus, F. prausnitzii, C. aerofaciens, E. sinensis, L. longoviformis*, and *R. intestinalis*). In certain embodiments, then present invention provides probiotic formulations containing live bacteria (e.g., from *O. splanchnicus, F. prausnitzii, C. aerofaciens, E. sinensis, L. longoviformis*, and *R. intestinalis*).

The present invention is not limited to the method used to identify the reduction (or non reduction) of bacteria of a selected genus (e.g., *Odoribacter, Faecalibacterium, Colinsella, Eggerthella, Lactonifactor*, and *Roseburia*) in a sample (e.g., stool sample) from a subject. The entire microbiome may be assayed to determine if there are other bacteria that are reduced or elevated in IC and IC/BPS. Exemplary methods include detecting 16s rRNA, PCR based methods, microarray, antibody based methods, and other suitable methods.

In certain embodiments, 16S rDNA sequence analyses is used to establish flora taxonomy (e.g., to determine if *Odoribacter, Faecalibacterium, Colinsella, Eggerthella, Lactonifactor*, and *Roseburia* is at reduced level in a particular stool sample). One exemplary approach to characterizing the GI microbiome relies upon 16S sequencing of stool and is as follows. Phylotype profiles of the microbiome populations may be generated using deep sequencing of, for example, the hypervariable V3-V5 region of the 16S ribosomal RNA (rRNA) gene, which has been validated by the HMP for use with human microbiomes and is one of the methods of choice for the HMP [PloS One, 2012, 7(6):p. e39315, herein incorporated by reference in its entirety]. Barcoding samples prior to sequencing (e.g., MiSeq tag sequencing) will yield approximately 50,000 reads/sample, ensuring detection of both dominant (core microbiome) and poorly represented taxa (variable microbiome). Identifying the existent taxa, diversity, and ecological relationships within each sample will generally entail processing large volumes of 16S DNA sequence data. The hypervariable V3-V5 region can be selectively amplified from total genomic DNA by 30 cycles of PCR using conserved primer sequences 357F (CCTACGGGAGGCAGCAG; SEQ ID NO:1) and 926R (CCGTCAATTCMTTTRAGT; SEQ ID NO:2) using protocols established by the HMP [PloS One, 2012, 7(6):p. e39315]. Amplicon pools can be quantified using a Qubit fluorimeter, and the average fragment sizes can be determined on an Agilent bioanalyzer High Sensitivity DNA LabChip (Agilent Technologies, Wilmington, Del.) and diluted to 10 nM. The 10 nM solution is checked for accuracy by qPCR. The amplicons are spiked with 20% of PhiX control library to provide a more balanced sample for accurate calculation of matrix, phasing and prephasing. The amplicons/PhiX mixture are sequenced on an Illumina MiSeq V2 sequencer for 250 nt from each end of the amplified fragments.

In certain embodiments, important OTUs (e.g., in addition to *Odoribacter, Faecalibacterium, Colinsella, Eggerthella, Lactonifactor*, and *Roseburia*) mediating UCPPS are identified using an unbiased protocol that incorporates machine learning and decision tree algorithms. In certain embodiments, a primary analyses will produce 16S rDNA amplicon (taxonomic) data, although secondary analyses may be performed. Data from the 16S sequencing experiments includes 16S rDNA amplicon sequences (OTUs), binned at 97% sequence identity (Schloss, et al., PLoS, Comput Bio, 2010, 6(7), herein incorporated by reference), OTU abundance profiles and phylogenic relationships between OTUs. Using this approach, one can relate important pieces of information to previously unrecognized species, genera, families, or even phyla that are driving or exacerbating UCPPS or maintaining health or find environmental variables that are affecting the microbial community dynamics. Downstream analyses utilizing various software tools (Qiime, Galaxy: Principal coordinate analysis (PCA) showing microbial community similarity, generation of OTU heatmaps, generation of phylogenetic trees and functional characteristics of microbial communities (PICRUSt). These analyses will not only indicate differences or similarities between microbial communities in UCPPS and control patients but also relate microbial communities to physiological functions. Finally, functional profiles of GI flora can be derived from 16S analyses using phylogenetic investigation of communities by reconstruction of unobserved states (PICRUSt (Langille et al., Nat. Biotech., 2013, 31(9):814-812, herein incorporated by reference). PICRUSt is a recently developed computational approach that recapitulates key findings of the Human Microbiome Project, in terms of metagenome profiles and inferred functional properties of the population, without the resource-intensive requirements typically associated with metagenomic profiling by shotgun sequencing. This in silico approach permits metagenomic assessment of each patient sample.

EXAMPLES

Example 1

Detection of Reduced *Odoribacter* in IC Patient Stool Samples

Stool and vaginal swab samples from female IC patients that were 18-50 years old were tested. 16S rDNA sequencing (MiSeq) was used to identify bacteria in the samples. In stool microbiota, cluster analysis segregated IC patients from healthy controls (HC). Many OTUs (operational taxonomic units) were significantly elevated/reduced in IC patients, relative to controls. Vaginal microbiota did not cluster by pain status. Analyses of stool microbiota revealed OTU112 (*Odoribacter*) as a taxon significantly reduced in IC patients as shown in FIG. 1A.

Figure 1B:
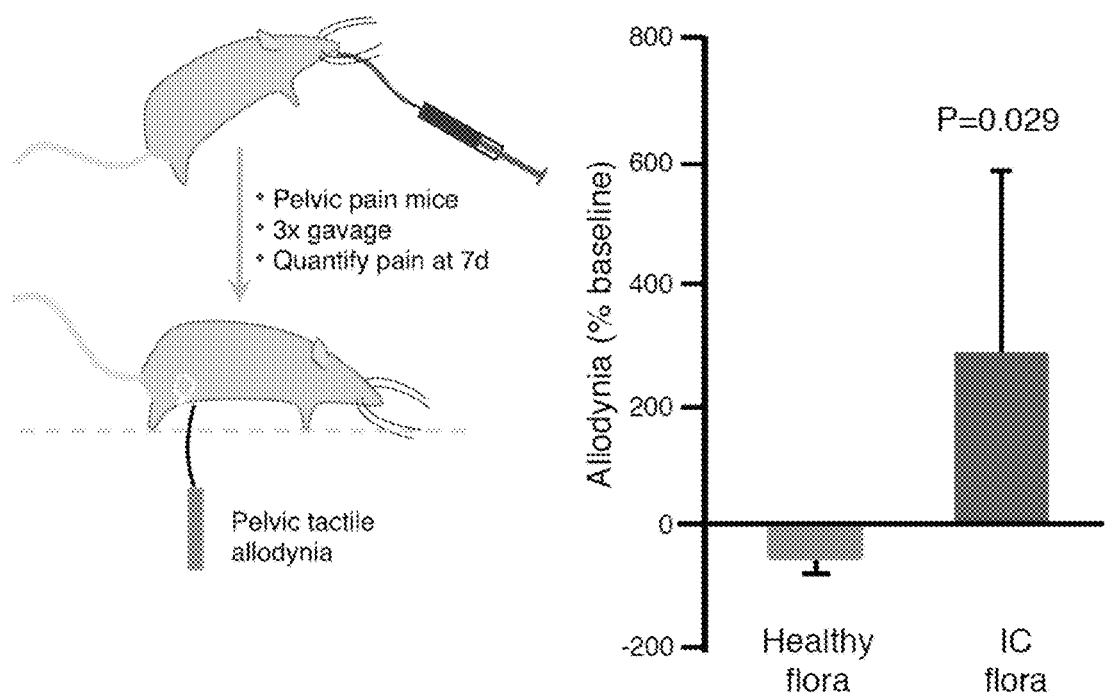

To determine whether stool microbiota modulate pelvic pain, anaerobic cultures of human stool were gavaged into mice in a murine model of chronic pelvic pain. Pain was quantified by assessing tactile allodynia after stool culture administration (3 administrations during 1 week). IC cultures significantly increased pelvic pain relative to healthy stool cultures (n=6-7) as shown in FIG. 1B.

Example 2

Identification of Genera of Bacteria Altered in Interstitial Cystitis (IC) Patients In certain studies, vaginal swabs and/or stool and from MAPP and non-MAPP IC patients and controls, and anaerobic cultures of duplicate samples were banked (n=34). No clear relationships emerged from three vaginal sites. In contrast, Random Forest analyses of operational taxonomic units (OTUs) in stool samples identified the genera of bacteria in Table 1 significantly associated with symptoms, indicating IC patients have altered bowel flora.

TABLE 1

Actinobacteria *Eggerthella*,
*Faecalibacterium*,
*Lactonifactor*,
Lachnospiracea incertae sedis,
*Clostridium*,
*Collinsella*,
*Roseburia*,
*Dorea*,
*Blautia*,
Proteobacteria *Escherichia Shigella*,
*Streptococcus*,
Lachnospiracea incertae sedis,
*Flavonifractor*,
*Blautia*,
Lachnospiracea incertae sedis,
*Anaerostipes*,
Erysipelotrichaceae incertae sedis,
Lachnospiracea incertae sedis,
*Anaerofilum*,
*Anaerofustis*,
*Faecalibacterium*,
*Faecalibacterium*,
Lachnospiracea incertae sedis A sample (e.g., stool sample) from a subject suspected of having IC (e.g., stool sample) can be screened to detect lower or higher levels of one of more of these genera of bacteria, such that a diagnosis of IC or related condition can be made. This allows the patient to be treated appropriately for IC, such as by providing probiotics with the type(s) of bacterial that are, for example, lower in the sample. Samples can be screened by quantitative PCR with primer specific for a particular genera of bacteria in Table 1 (e.g., primers to conserved regions in a particular genera or primer to a particular species in one of the genera).

Example 3

Figure 2:
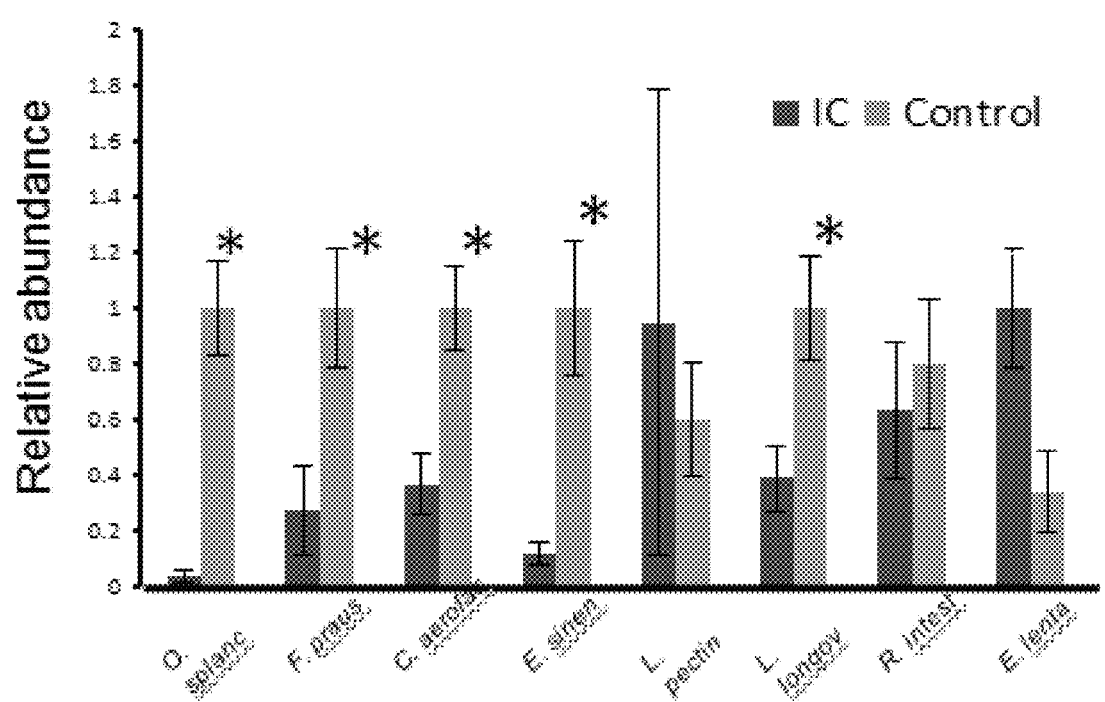
FIG. 2 shows that certain species of bacteria have lower or higher prevalence in stool samples from IC patients compared to controls. The data in FIG. 2 shows results of qPCR assays to measure the relative abundance of such bacteria.

Identification of Six Species of Bacteria Altered in Interstitial Cystitis (IC) Patients In certain studies, species-specific primer pairs were developed for each species within certain highly ranked OTUs from ERF analyses. Each primer pair was then tested for amplicon specificity by melt curve analysis of amplification products using a small panel of stool DNAs purified from healthy controls. Primer pairs were used for qPCR of stool DNA from IC patients and controls, and five significant species were identified: *O. splanchnicus, F. prausnitzii, C. aerofaciens, E. sinensis,* and *L. longoviformis* (FIG. 2; $P<0.05$). A sixth species, *R. intestinalis*, was also identified as lower in IC patients (see FIG. 2). The primer pairs for these six species are shown in Table 3:

TABLE 3

| Bacterial Species | Forward Primer | SEQ ID NO: | Reverse Primer | SEQ ID NO: |
| --- | --- | --- | --- | --- |
| *O. splanchnicus* | TCG AAG GCT TGA CCT TAC GC | 3 | TTC ATT CGT ACG TCC GGT GG | 4 |
| *F. prausnitzii* | GAG GTT GAA CGG CCA CAT TG | 5 | ACC TAG TAA ACA TCG GCC AC | 6 |
| *C. aerofaciens* | GTG GAA CAC CGA TGG CGA A | 7 | CCT GGT AAG GTT CTT CGC GT | 8 |
| *E. sinensis* | GGG ATC TCT AAT CCG AGG GC | 9 | TAA TGC GTT AGC TGC GGG C | 10 |
| *L. longoviformis* | TGC ATT GGA AAC TGT GCA GC | 11 | TTC TTG CGA ACG TAC TCC CC | 12 |
| *R. intestinalis* | CGG CTT AAA TAC GTG CCA GC | 13 | AGC CTC AGC GTC AGT AAT CG | 14 |

Interestingly, since these species are all Deficient in Interstital Cystitis Pelvic Pain (DIPP), DIPP strain deficiency may result in diminished or altered microbiota function and thus may contribute directly or indirectly to IC symptoms. These identified species are therefore candidates for oral probiotic therapy to complement any functional defect(s). For example, probiotics that contains one to all six of these bacterial species (e.g., to increase the level of such species in the gut of the subject to help reduce symptoms of IC). Moreover, it was found, for *O. splanchnicus, F. prausnitzii, C. aerofaciens, E. sinensis,* and *L. longoviformis*, that these species have area under the curve (AUC) consistent with high sensitivity and specificity by ROC analyses (Table 2).

TABLE 2

DIPP species are putative IC biomarkers.

| DIPP Species | AUC (mean) |
| --- | --- |
| *Colinsella aerofaciens* | 0.86 |
| *Eggerthella sinensis* | 0.84 |
| *Faecalibacterium prasunitzii* | 0.79 |
| *Odoribacter splanchnicus* | 0.72 |
| *Lactonifactor longoviformis* | 0.55 |

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A probiotic formulation comprising at least three species of live bacteria from the genera of bacteria selected from the group consisting of: *Odoribacter, Faecalibacterium, Collinsella, Eggerthella, Lactonifactor,* and *Roseburia*, wherein at least two species are selected from the group consisting of: *Odoribacter splanchnicus, Collinsella aerofaciens, Eggerthella sinensis, Lactonifactor longoviformis,* and *Roseburia intestinalis*.

2. The probiotic formulation of claim 1, comprising at least three species selected from the group consisting of: *Odoribacter splanchnicus, Faecalibacterium prausnitzii, Collinsella aerofaciens, Eggerthella sinensis, Lactonifactor longoviformis,* and *Roseburia intestinalis*.

3. The probiotic formulation of claim 2, comprising at least four species selected from the group consisting of: *Odoribacter splanchnicus, Faecalibacterium prausnitzii, Collinsella aerofaciens, Eggerthella sinensis, Lactonifactor longoviformis,* and *Roseburia intestinalis*.

4. The probiotic formulation of claim 3, comprising at least five species selected from the group consisting of: *Odoribacter splanchnicus, Faecalibacterium prausnitzii, Collinsella aerofaciens, Eggerthella sinensis, Lactonifactor longoviformis,* and *Roseburia intestinalis*.

5. The probiotic formulation of claim 4, comprising *Odoribacter splanchnicus, Faecalibacterium prausnitzii, Collinsella hella sinensis, Lactonifactor longoviformis,* and *Roseburia intestinalis*.

6. The probiotic formulation of claim 1, further comprising a capsule formulated for human consumption with the live bacteria contained therein.

7. A kit comprising the probiotic formulation of claim 1, and a therapeutic agent for the treatment of interstitial cystitis.

* * * * *